United States Patent [19]

Frederick

[11] Patent Number: 4,915,686
[45] Date of Patent: Apr. 10, 1990

[54] IMPLANT INJECTION DEVICE

[75] Inventor: Mervyn J. Frederick, Eh Oss, Netherlands

[73] Assignee: Akzo N.V., Arnhem, Netherlands

[21] Appl. No.: 225,451

[22] Filed: Jul. 28, 1988

[30] Foreign Application Priority Data

Aug. 18, 1987 [NL] Netherlands .................. 8701934

[51] Int. Cl.⁴ .......................................... A61M 37/04
[52] U.S. Cl. .................................................. 604/60
[58] Field of Search ................. 604/57, 59, 60–63, 604/207–210, 220, 227

[56] References Cited

U.S. PATENT DOCUMENTS

| | | | |
|---|---|---|---|
| 2,513,014 | 6/1950 | Fields | 604/60 |
| 3,337,095 | 8/1967 | Marbach et al. | 604/208 X |
| 4,451,253 | 5/1984 | Harman | 604/60 |
| 4,597,753 | 7/1986 | Turley | |
| 4,643,723 | 2/1987 | Smits | 604/207 |
| 4,657,533 | 4/1987 | Oscarsson | 604/60 |

FOREIGN PATENT DOCUMENTS

WO8400304 2/1984 PCT Int'l Appl. .

Primary Examiner—Dalton L. Truluck
Attorney, Agent, or Firm—William M. Blackstone; John W. Schneller

[57] ABSTRACT

The invention relates to an injection device, in particular for once-only use, for injecting an implant which can release a drug in a controlled manner, which device comprises a housing which is provided at the injection end with an injection needle in which the implant can be disposed and in which a passage opening is disposed at the actuating end of the housing for a plunger, mounted in the housing and displaceable in the axial direction of the needle, which, on the one hand, can interact with the implant and, on the other hand, is provided with an actuating element, which element is constructed as an element for pressing and supporting against or on the part of the body to be treated.

36 Claims, 6 Drawing Sheets fig. 1 fig. 2 fig.7 fig.6 fig.8 fig.13 fig. 14 fig. 16 fig. 15

IMPLANT INJECTION DEVICE

The invention relates to an injection device, in particular for once-only use, for injecting an implant which can release a drug in a controlled manner, which device comprises a housing which is provided at the injection end with an injection needle in which the implant can be disposed and in which a passage opening is disposed at the actuating end of the housing for a plunger, mounted in the housing and displaceable in the axial direction of the needle, which, on the one hand, can interact with the implant and, on the other hand, is provided with an actuating element.

Such devices are known and are being used to an increasing extent for disposing, beneath the skin of the human body, a holder containing drugs which are gradually released over a relatively long time, for example a few weeks to a few years, to the body. In view of the usually great importance of such injections, they have to be carried out extremely accurately and carefully so that the implant is disposed in the correct position and manner beneath the skin and the satisfactory action of the drugs concerned is guaranteed. It is not satisfactorily possible to meet the requirements set using the known injection devices, inter alia, that which is described in WO 84/00304.

The object of the invention is to provide an injection device of the type mentioned in the introduction in which very high requirements as regards accurate injection and satisfactory action of the drugs are met over the required time. According to the invention, the injection device is characterized by the fact that the actuating element is constructed as an element for pressing and supporting against or on the part of the body to be treated, the supporting element being formed by a supporting surface, preferably provided with transverse ribs, whose surface area is 1 to 10 cm$^2$, in particular 2-5 cm$^2$. According to the invention, an embodiment of the injection device to be chosen is characterized by the fact that the supporting surface is elongated and extends in the longitudinal direction and at some radial distance from the plunger, and in that the pressing element is formed by a pressing surface, preferably provided with transverse ribs, which is disposed on the plunger opposite the supporting surface. Advantageously, according to the invention, the supporting surface is situated at an acute angle ($\alpha$) of the size of, for example, approximately 5° to the longitundinal direction of the plunger. The use of the device according to the invention is improved if the outside surface of the housing has over at least a section of its length one or more essentially flat surface. These flat surfaces may be disposed in a manner such that the housing has an approximately polygonal section, for example hexagonal, transversely to its longitudinal direction.

According to the invention, a beneficial embodiment of the injection device is characterized by the fact that the housing and the plunger are provided with stop elements which interact with each other and which are constructed in a manner such that the distance over which the plunger can be displaced in the hollow needle towards the extremity thereof is limited. According to the invention, the housing and the plunger are advantageously linked to each other via a coupling which, in the closed coupled state, links the housing and the plunger immovably to each other and, in the opened decoupled state, permits movement of the plunger in the housing and in the hollow needle. According to the invention, one half of the coupling is in this case formed at the end of the said supporting surface of the plunger facing the needle.

The injection device according to the invention is advantageously characterized by the fact that the housing which is moulded from a thermoplastic material, in particular polyacetal, polyethylene, polypropylene or the like, is provided with a cylindrical axial bore adjoining the hollow metal needle. In addition the plunger also which is moulded from a thermoplastic material, is preferably disposed so as to be axially displaceable in the bore of the housing and in the hollow needle. Further the actuating element of the plunger is preferably provided with pressing and supporting surfaces situated opposite each other in a diametrically oblique manner with respect to the plunger axis. The plunger also has at the actuating end, a first section with a large diameter which fits into the bore of the housing and at the injections end, a second section with a smaller diameter which fits into the hollow needle.

The invention also comprises the injection device described which is provided with, in particular, an elongated, implant which can release a drug in a controlled manner. According to the invention, the implant is preferably made of a polymer such as polysiloxane, polyalkylene or polylactide, in which the drug is homogeneously dispersed or which encases the drug.

The invention also comprises the sterilized device which is disposed in a closed packaging, inaccessible to bacteria, formed preferably from a transparant thermoplastic material or from aluminium foil. If the needle in the packaging contains the implant and is provided in the packaging contains the implant and is provided with a protective cap, the injection device can be carefully manufactured commercially in its entirety in this packaged form even in large numbers. In this case, in carrying out the injection, it is necessary only to remove the packaging, provided, for example, with a tear strip, and the protective cap from the needle. In other words, at the treatment site, the operations to be carried out by the doctor or nurse involved are limited to a minimum. Risks of infection are excluded by the onceonly use of the device according to the invention. Infections and transferable diseases are avoided by the once-only use, especially in the treatment of fairly large groups of people. As a result of the practical and simple construction of the injection device according to the invention with the pressing and supporting elements described, the injection device can easily be pressed and supported with one hand on the body to be treated, while the other hand is free. Further after injecting the needle with the implant therein, the injection device can be used for possibly opening the coupling between plunger and housing and for withdrawing the needle form the body. In this process, the implant is simultaneously pushed by the free extremity of the plunger out of the hollow needle, as a result of which the implant remains behind in the body. The construction of the injection device according to the invention with the stop elements on the housing and plunger has the advantage that, during injection of the needle with the implant, undesirable premature movement of the implant in the hollow needle can be prevented. In particular, as a result of this, it is possible to prevent, with the injection device according to the invention, the implant from being pushed during the insertion of the needle in the body by the plunger wholly or partially outwards from the needle with all the disadvantages thereof such as, for example, the breaking off of the implant or the excessively deep insertion of the implant. All this has the consequence that, with the simple injection device according to the invention, the injection of an implant, which is important to an increasing extent, can be carried out particularly accurately and carefully. The satisfactory action and the accuracy of the injection device according to the invention are improved still further if the housing and the plunger are linked to each other in the manner described via a coupling.

The invention also comprises a method for inserting an implant in a body, which implant can release a drug in a controlled manner, the injection device described and according to the invention being used.

The invention will be explained in more detail by reference to the diagrammatic drawing.

Figure 1:
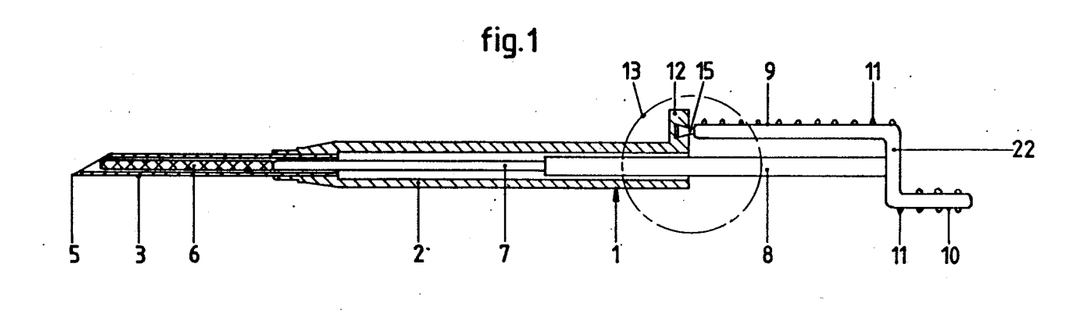
FIG. 1 shows the injection device according to the invention with lock or coupling.
Figure 2:
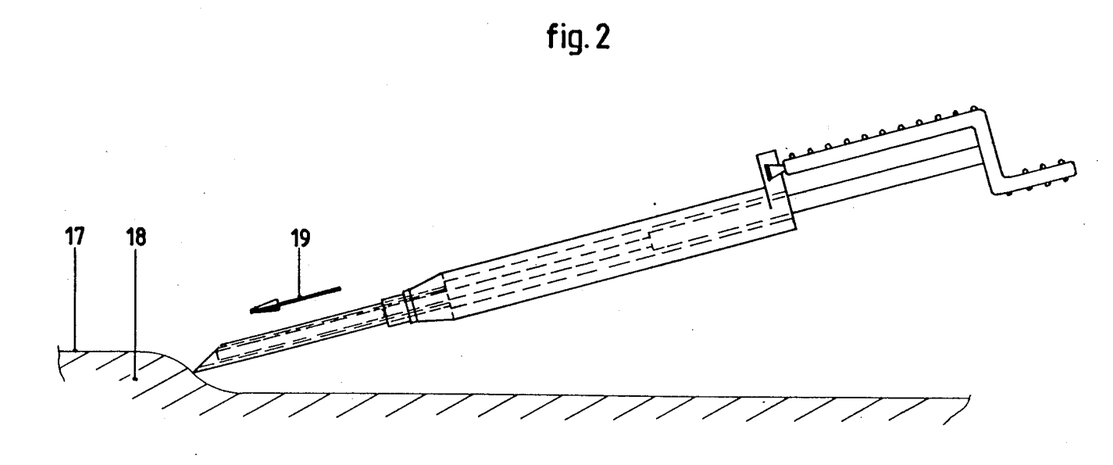
FIG. 2-5 show the device according to FIG. 1 in various states during use.
Figure 8:
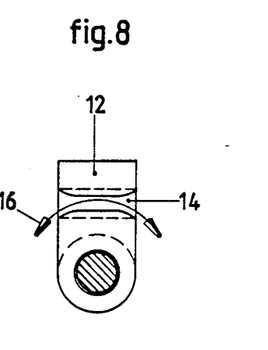
Figure 9:
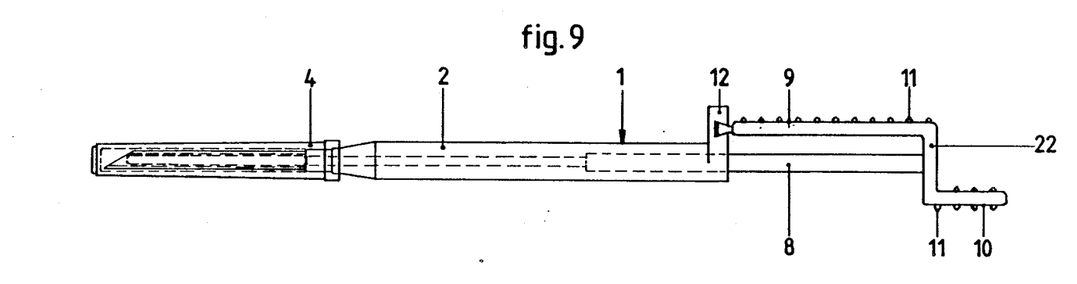
FIG. 9 shows an actual construction of the injection device according to the invention in elevation.

FIG. 1 shows, in longitudinal section, a first embodiment of the injection device according to the invention, indicated in general by 1, which contains a housing 2 and an injection needle 3 attached thereto, from which the protective cap 4 shown in FIG. 9 has been removed. The packaging for the injection device 1 has also already been removed in FIG. 1. Just in front of the start of the sloping point 5 of the needle 3 there is located therein a cylindrical implant 6 which contains a drug to be released in a controlled manner. Furthermore, the housing 2 contains an axially displaceable and rotatable plunger therein, which, at the injection end of the device 1, has a cylindrical section 7 with smaller diameter and, at the actuating end of the device, has a cylindrical section 8 with larger diameter. The plunger section 7 with smaller diameter rests against and can interact with the implant 6, for which purpose plunger section 7 fits into the hollow needle 3 with a fit which permits axial movement. The plunger section 8 with larger diameter is mounted in the housing 2 with a fit which permits axial movement. At the end facing away from the needle 3, the plunger is provided with an actuating element which, in the embodiment according to FIG. 1, is constructed with a supporting element in the form of the supporting surface 9 and a pressing element in the form of the pressing surface 10. The supporting surface 9 and the pressing surface 10 both form flat surfaces which are provided with ribs 11 and which are attached obliquely and diametrically opposite each other to the plunger section 8. On the housing 2 an upright projection 12 is formed which interacts with the end of the supporting surface 9 to form an axial stop to limit the maximum distance over which the plunger and the housing can be displaced towards each other. In the state according to FIGS. 1 and 2, the housing 2 and the plunger 7, 8 are linked to each other via a coupling or lock between parts of the projection 12 and the pressure surface 9 which interacts with each other in the zone 13 encircled by a broken line. The circled zone 13 of the injection device is drawn for clarification on a larger scale in FIGS. 6, 7 and 8. In order to bring about the coupling between the housing 2 and the plunger 7, 8, the projection is provided with a groove 14, to some extend following a circle, having a cross section with a swallow-tail shape. As can be seen from the front view in FIG. 6 and the plan view in FIG. 7, the supporting surface 9 rigidly linked to the plunger is provided with a projection 15 having a cross section which is also of swallow-tail shape and which engages in the groove 14 in an embodiment having a closed coupling or lock as shown in FIGS. 1, 2, 6 and 7. In the closed state of the coupling or the lock, the housing and the plunger are linked to each other immovably in the axial direction. This linking between housing and plunger can be broken by opening the coupling, which can be done by rotating the plunger around its axis in the direction of the arrow 16 indicated in the side view of FIG. 8, in the process of which the projection 15 is released from the groove 14.

Figure 3:
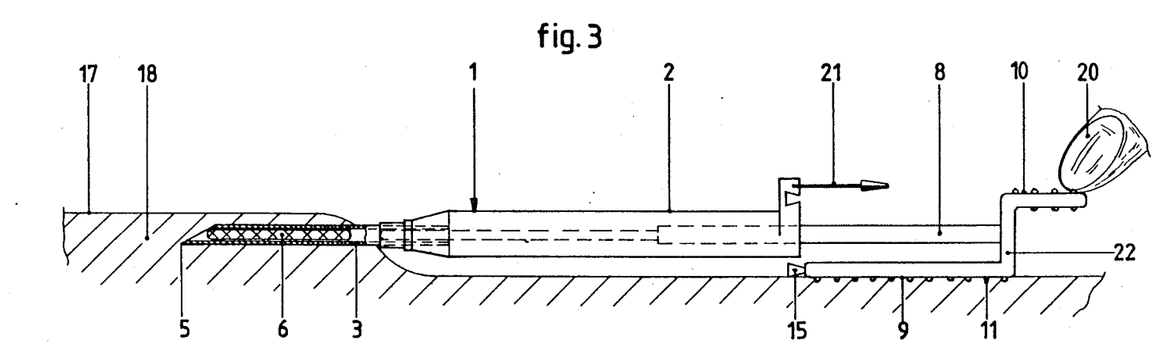
Figure 4:
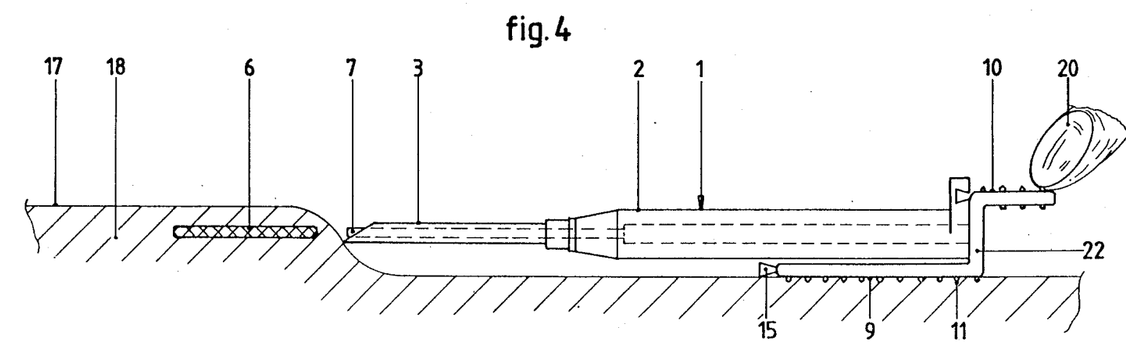
Figure 5:
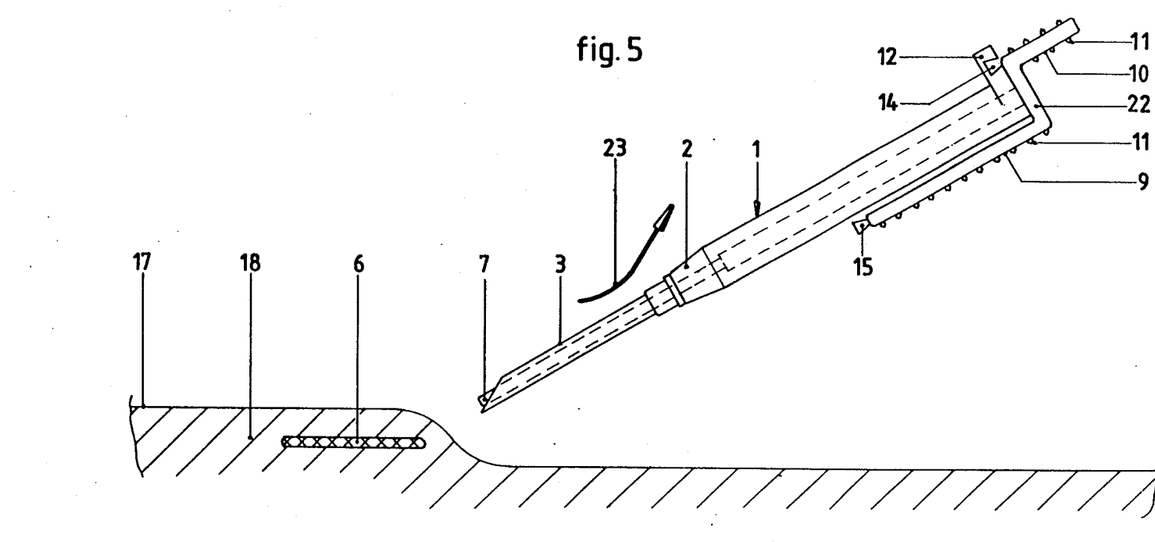
Figure 6:
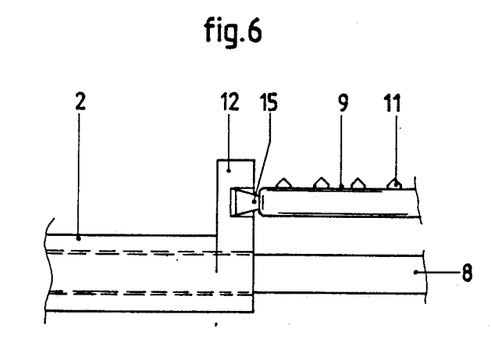
FIGS. 6-8 show, on a larger scale, the construction of the lock or the coupling in the device according to FIGS. 1-5.
Figure 7:
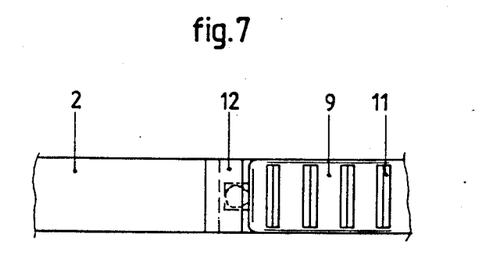

FIGS. 2-5 indicate diagrammatically the course of events during the insertion of the implant 6 beneath the skin of the body 18 of a patient. In this process, the point of the needle 3 of the device 1 is placed at the desired point of the skin 17 (FIG. 2) and then the complete device 1 is displaced axially in the direction of the arrow 19, the needle 3 with the implant 6 therein being inserted over the length of the needle into the body 18 beneath the skin 17. The above mentioned situation is shown in FIG. 3. After the needle 3 with the implant 6 therein has reached the subcutaneous position according to FIG. 3, the coupling between the housing 2 and the plunger 7, 8 is opened by rotating the plunger 1800° about its axis, in the process of which the projection 15 is released from the groove 14 and the supporting surface 9 and the pressing surface 10 reach the position shown in FIG. 3 with respect to the skin. Then the pressing surface 10 is pressed downwards with one hand 20, as a result of which the large supporting surface 9 is firmly pressed on the skin 17 thereby supporting the plunger in place. Then the housing 2 is slid axially over the plunger in the direction of the arrow 21 using the other hand. During the last metioned sliding movement, the housing 2 and the needle 3 firmly attached to it are withdrawn from the body 18. Immediately after the needle 3 has left the body 18, the projection 12, which also acts as a stop, comes up against the linking piece 22 of the supporting surface 9 and the pressing surface 10 (see FIG. 4). During the last mentioned withdrawal of the needle 3, the section 7 of the plunger gradually drives the implant 6 out of the needle, as a result of which the implant is deposited in the body as the needle leaves the body. The device 1 can then be removed in the direction of the arrow 23 (see FIG. 5) and be destroyed since it is intended for once-only use.

Figure 10:
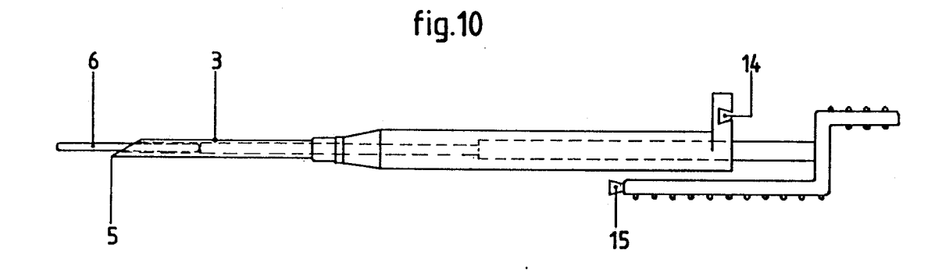
FIG. 10 shows the device according to FIG. 9 in the state during the withdrawal of the needle.
Figure 11:
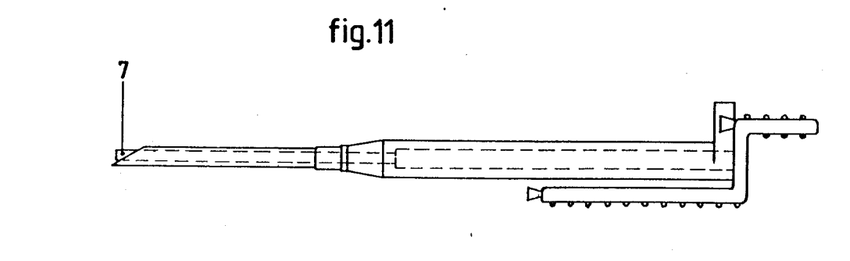
FIG. 11 shows the device according to FIG. 9 in the state following the complete withdrawal of the needle and following the injection of the implant.

In order to give a still clearer picture of the practical construction and the design, the injection device according to the invention of the type according to FIGS. 1–8 is again shown in elevation in various situations in FIGS. 9, 10 and 11. FIG. 9 in this case shows the injection device in the same position as is shown in section in FIG. 1, but with the needle provided with a protective cap 4. FIG. 10 shows the injection device in an intermediate state in which approximately half of the needle may be withdrawn from the body. FIG. 11 shows the injection device in the state in which the needle may have been withdrawn completely from the skin, which state corresponds to FIG. 4.

Figure 12:
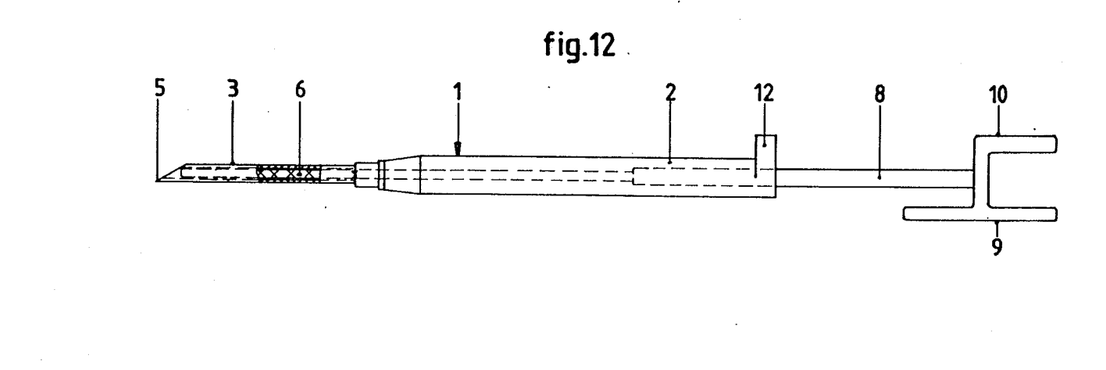
FIGS. 12 and 13 show two somewhat modified embodiments in which no lock or cou*;ong are disposed between the plunger and the housing.
Figure 13:
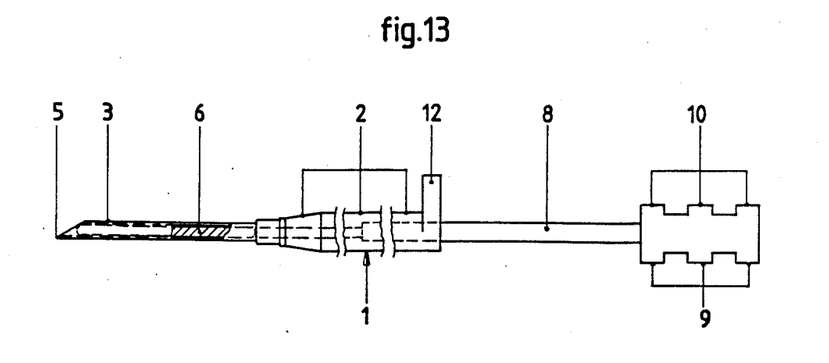

FIGS. 12 and 13 show somewhat modified embodiments of the injection device 1 according to the invention, in which corresponding parts have been indicated with the same reference numerals. The most important difference of the two devices shown in FIGS. 12 and 13 from that according to FIGS. 1–11 is that the device according to FIGS. 12 and 13 lacks the coupling or the lock between the housing 2 and the plunger 7, 8. In the device according to FIG. 12, supporting surface 9 has a smaller surface area than in the device according to FIGS. 1–11, which may be of practical importance in situations in which little space is present for the supporting surface. In the device according to FIG. 13, the pressing surface 10 and the supporting surface have an equally large square surface area.

Figure 14:
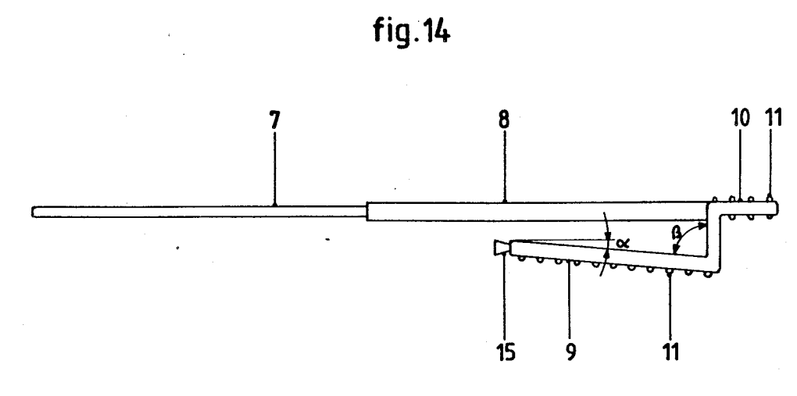
FIG. 14 shows a construction with the supporting surface in another position.

FIG. 14 shows a somewhat different embodiment in which the supporting surface 9 is situated obliquely, i.e. at an acute angle $\alpha$ of, for example, approximately 5° with respect to the longitudinal axis of the plunger 7, 8. The angle $\beta$ between the supporting surface 9 and the linking piece 22 is also then acute and is approximately 85°.

Figure 15:
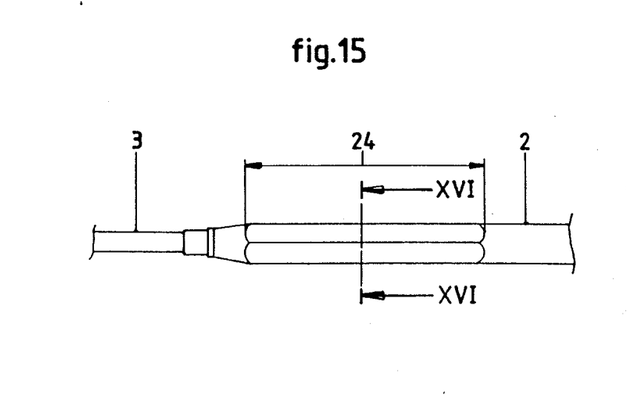
FIG. 15 and 16 show an embodiment in which the housing has a hexagonal section.
Figure 16:
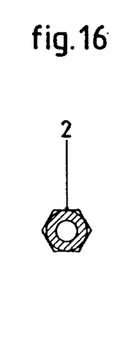

FIG. 15 with the associated outline of the cross section at the point XVI—XVI shown FIG. 16 shows an embodiment in which the periphery of the housing 2 has a hexagonal cross section over the section 24 of the length. The outline of the housing 2 has, as a result of this, six flat surfaces over the length 24, as a result of which the use of the device according to the invention is improved. Of course, instead of a hexagonal section, a more or less truncated or another polygonal cross section such as a retangle can also be used.

Various modifications can be made within the scope of the invention. In particular, couplings or lacks of another type may be disposed between the housing and the plunger.

We claim:

1. An injection device for injecting a controlled drug release implant beneath a subject's skin, comprising:
   a housing, said housing having an injection needle mounted on one end thereof and collinearly therewith to form a single unit, both said housing and needle having hollow, communicating centers:
   an implant being disposed within the hollow center of the housing and needle unit, and
   a plunger disposed within the hollow center of said housing and displaceable in an axial direction toward said needle to interact with said implant and provided with an actuating element, said actuating element including means extending axially on opposite sides of said element for alternately supporting and pressing said element against or on skin to be treated so as to maintain said plunger in a steady position with respect to said implant despite collinear relative movement of said housing and needle unit.

2. Device according to claim 1, wherein the actuating element comprises a supporting surface for pressing and supporting against the skin of the subject having a surface area of about 1 to 10 cm$^2$.

3. Device according to claim 2, wherein the supporting surface is elongated and extends in the longitudinal direction and at some radial distance from the plunger.

4. Device according to claim 3, wherein the supporting surface is situated at an acute angle ($\alpha$) with respect to the longitudinal direction of the plunger.

5. Device according to claim 2, comprising a pressing element disposed on the plunger opposite the supporting surface.

6. Device according to claim 1, wherein the housing has an outside surface with one or more essentially flat surfaces.

7. Device according to claim 6, wherein the flat surfaces are disposed in a manner such that the housing has a polygonal cross section.

8. Device according to claim 1, wherein the housing and the plunger are provided with stop elements which interact with each other and which are constructed in a manner such that the distance over which the plunger can be displaced in the hollow needle toward the extremity thereof is limited.

9. Device according to claim 1, wherein said housing and said plunger are linked to each other via a coupling which, in a closed state, links said housing and said plunger immovably to each other and, in an open state, permits collinear movement of said plunger within said housing and said hollow needle.

10. Device according to claim 9, wherein one half of the coupling is formed at the end of a supporting surface for the plunger.

11. Device according to claim 1, wherein the housing, is moulded from a thermoplastic material, is provided with a cylindrical axial bore adjoining the hollow metal needle, the plunger is moulded from a thermoplastic material, is disposed so as to be axially displaceable in the bore of the housing and in the hollow needle, and the actuating element of the plunger is provided with pressing and supporting surfaces situated opposite each other in a diametrically oblique manner with respect to the plunger axis.

12. Device according to claim 11, wherein the plunger has, at the actuating end, a first section with a large diameter which fits into the bore of the housing and, at the injection end, a second section with a smaller diameter which fits into the hollow needle.

13. Device according to claim 7 wherein the device is provided with an implant which can release a drug in a controlled manner.

14. Device according to claim 13, wherein the implant is formed by a polymer in which the drug is dispersed or which encases the drug.

15. Device according to claim 1, wherein the device is sterilized and is disposed in a closed packaging that is inaccessible to bacteria.

16. Device according to claim 1, wherein the supporting surface has transverse ribs formed in the surface thereof that is placed against the skin of the subject to be treated.

17. Device according to claim 5, wherein the surface of the pressing element has transverse ribs formed therein.

18. Device according to claim 11, wherein the thermoplastic material is a polyacetal polymer.

19. Device according to claim 14, wherein the polymer is selected from the group consisting of polysiloxane, polyalkylene and polylactide.

20. Injection device for injecting a controlled drug release implant beneath a subject's skin, comprising a housing having an injection needle mounted on one end thereof and collinearly therewith to form a single housing and needle unit, both the housing and needle having hollow, communicating centers;

an implant being disposed within the hollow center of the housing and needle unit;

a plunger extending in a longitudinal direction within the hollow center of the housing, being displaceable in an axial direction toward said needle to interact with the implant and including an actuating element, said actuating element comprising a supporting surface for pressing and supporting against the skin of the subject having and a pressing element disposed on the plunger opposite said supporting surface, said housing and said plunger being linked to each other via coupling means which, in a closed state, links said housing and said plunger immovably to each other and, in an open state, permits collinear movement of said plunger within said housing and said hollow needle.

21. Device according to claim 22, wherein said supporting surface for pressing and supporting against the skin of the subject has a surface area of about 1 to 10 cm$^2$.

22. Device according to claim 20, wherein said supporting surface is elongated and extends in said longitudinal direction and at a given radial distance from said plunger.

23. Device according to claim 22, wherein the supporting surface is situated at an actue angle ($\alpha$) with respect to the longitudinal direction of the plunger.

24. Device according to claim 20, wherein said housing has an outside surface with one or more essentially flat surfaces.

25. Device according to claim 24, wherein said flat surfaces are disposed in a manner such that said housing has a polygonal cross section.

26. Device according to claim 20, wherein the housing and the plunger are provided with stop elements which interact with each other and which are constructed in a manner such that the distance over which the plunger can be displaced in the hollow needle toward the extremity thereof is limited.

27. Device according to claim 20, wherein one half the coupling is formed at the end of a supporting surface for the plunger.

28. Device according to claim 20, wherein the housing is moulded from a thermoplastic material, is provided with a cylindrical axial bore adjoining the hollow metal needle, the plunger is moulded from a thermoplastic material, is disposed so as to be axially displaceable in the bore of the housing and in the hollow needle, and the actuating element of the plunger is provided with pressing and supporting surfaces situated opposite each other in a diamterically oblique manner with respect to the plunger axis.

29. Device according to claim 20, wherein the plunger has, at the actuating end a first section with a large diameter which fits into the hollow needle.

30. Device according to claim 25, wherein the device is provided with an implant adapted to release a drug in a controlled manner.

31. Device according to claim 30, wherein the implant is formed by a polymer in which the drug is dispersed or which encases the drug.

32. Device according to claim 20, wherein the device is sterilized and is disposed in a closed packaging that is inaccessible to bacteria.

33. Device according to claim 20, wherein the supporting surface has transverse ribs formed in the surface thereof that is placed against the skin of the subject to be treated.

34. Device according to claim 20, wherein the surface of the pressing element has transverse ribs formed therein.

35. Device according to claim 28, wherein the thermoplastic material is polyactetal polymer.

36. Device according to claim 31, wherein the polymer is selected from the group consisting of polysiloxane, polyalkylene and polyactide.

* * * * *

UNITED STATES PATENT AND TRADEMARK OFFICE
CERTIFICATE OF CORRECTION

PATENT NO. : 4,915,686

DATED : April 10, 1990

INVENTOR(S) : Mervyn J. Frederick and Wilhelm Engelinus Koenen

It is certified that error appears in the above-identified patent and that said Letters Patent is hereby corrected as shown below:

Title Page:

Item [19], "Frederick" should read --Frederick et al--.

Item [75] Inventor: "Mervyn J. Frederick, Eh Oss, Netherlands" should read
--Mervyn J. Frederick, Eh Oss; Wilhelm E. Koenen,
PN Ravenstein, both of the Netherlands--.

Signed and Sealed this

Seventh Day of January, 1992

Attest:

HARRY F. MANBECK, JR.

*Attesting Officer*      *Commissioner of Patents and Trademarks*